US00PP23891P2

(12) United States Plant Patent
Hansen

(10) Patent No.: US PP23,891 P2
(45) Date of Patent: Sep. 10, 2013

(54) ***BAPTISIA* PLANT NAMED 'BLUEBERRY SUNDAE'**

(50) Latin Name: ***Baptisia* hybrid**
Varietal Denomination: Blueberry Sundae

(75) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 88 days.

(21) Appl. No.: 13/374,345

(22) Filed: Dec. 22, 2011

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Baptisia*, 'Blueberry Sundae' characterized by its flowers that are blue in color and held on erect flower stems, its densely branched, uniform and upright plant habit, its vigorous growth rate and hardiness in U.S.D.A. Zones 4 to 8.

2 Drawing Sheets

Botanical classification: *Baptisia* hybrid.
Cultivar designation: 'Blueberry Sundae'.

BACKGROUND OF THE INVENTION

The present invention relates to a new and distinct cultivar of hybrid *Baptisia* plant, botanically an interspecific hybrid in origin and known as *Baptisia* 'Blueberry Sundae' and will be referred to hereafter by its cultivar name, 'Blueberry Sundae'. The new cultivar represents a new false indigo, an herbaceous perennial grown for landscape use.

The new invention arose from an ongoing controlled breeding program in Waseca, Minn. The breeding program was established by the Inventor in 1998 with the goal of developing *Baptisia* hybrids with unique flower colors and plant habits.

'Blueberry Sundae' was derived from an F1 cross made in 2003 between an unnamed plant of *Baptisia minor* as the female parent and an unnamed plant of *Baptisia australis* as the male parent. 'Blueberry Sundae' was selected in 2007 as a single plant amongst the resulting seed progeny.

Asexual reproduction of the new cultivar was first accomplished by stem cuttings in 2008 in Zeeland, Mich. under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar as observed for five years in Waseca, Minn. These attributes in combination distinguish 'Blueberry Sundae' from other varieties of *Baptisia* known to the Inventor.

1. 'Blueberry Sundae' exhibits flowers that are blue in color.
2. 'Blueberry Sundae' exhibits blue-green foliage.
3. 'Blueberry Sundae' has a vigorous upright and uniform plant habit intermediate in size and habit between the parent plants.
4. 'Blueberry Sundae' is hardy in U.S.D.A. Zones 4 to 8.

In comparison to the female parent, *Baptisia minor*, 'Blueberry Sundae' has a larger more vigorous growth habit and produces more foliage and flower stems. In comparison to the male parent, *Baptisia australis*, 'Blueberry Sundae' has a more upright, compact growth habit and greater uniformity. The closest comparison variety *Baptisia australis* 'Big Ben' (not patented) has flowers that are more blue-violet in color and matures into a much larger plant in height and width. Another comparison plant is *Baptisia* 'Twilite' (U.S. Plant Pat. No. 19,011). Also an interspecific hybrid, it produces violet-purple colored flowers and reaches a much larger plant size in height and width. An additional comparison plant is *Baptisia* 'Purple Smoke' (not patented); an interspecific hybrid having violet colored flowers, charcoal gray stems, and an upright habit.

BRIEF DESCRIPTION OF THE DRAWING

The accompanying colored photographs illustrate the overall appearance and distinct characteristics of the new *Baptisia*. The photographs were taken of plants and plant parts of a plant five years in age as grown outdoors in Waseca, Minn.

The photograph in FIG. 1 is a view of a plant of 'Blueberry Sundae' in bloom and illustrates the uniform habit and the abundance of flowers stems.

Figure 1:
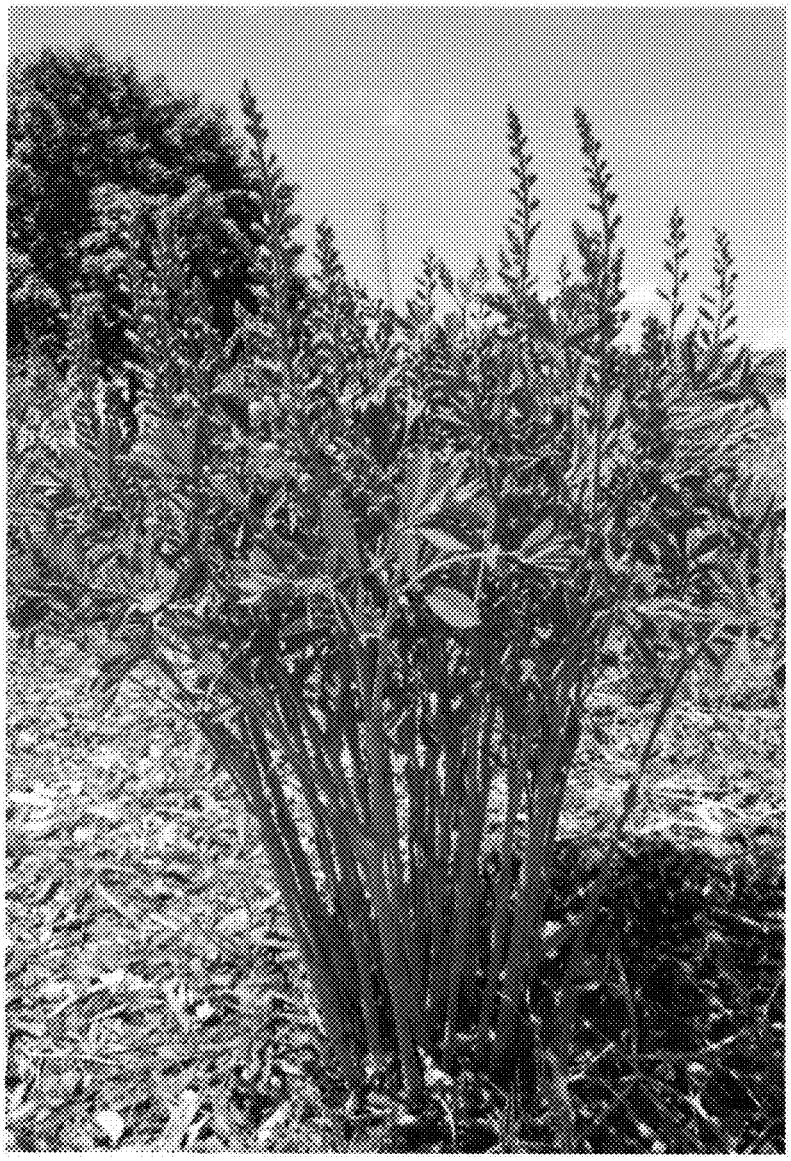
Figure 2:
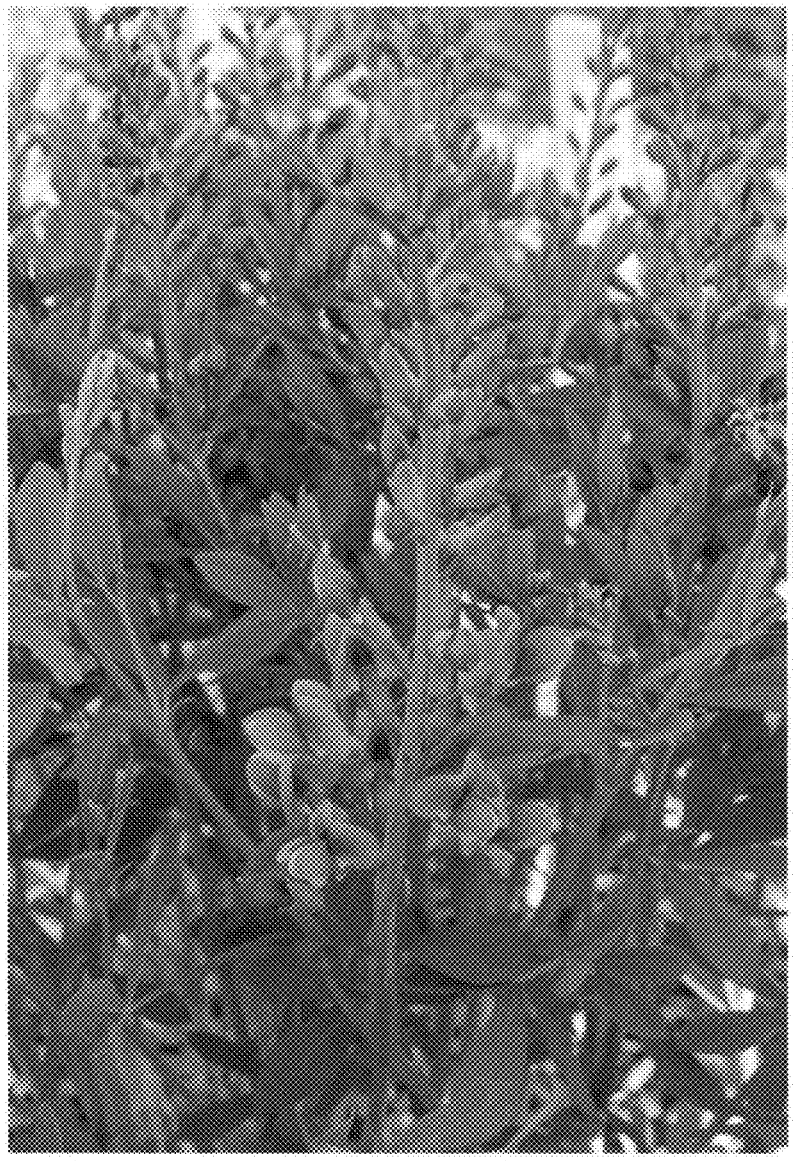

The photograph in FIG. 2 is of a close-up view of the flowers of 'Blueberry Sundae'.

The colors in the photographs are as close as possible with the photographic and printing technology utilized. The color values cited in the detailed botanical description accurately describe the colors of the new *Baptisia*.

DETAILED BOTANICAL DESCRIPTION OF THE PLANT

The following is a detailed description of 5 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early June through early July in Waseca, Minn. (typically June 8th through June 12th).

*Plant habit.*—Vase-shaped with flower racemes partially in foliage.

*Height and spread.*—Reaches about 83 cm width and 81 cm in height.

*Hardiness.*—U.S.D.A. Zones 4 to 8.

*Culture.*—Prefers well-drained to medium moist soils in full sun, tolerant to lean soils and drought.

*Diseases and pests.*—No susceptibility to diseases or pests has been observed.

*Root description.*—Deep rooted, fibrous.

Growth and propagation:

*Propagation.*—Stem cuttings is the preferred method, tissue culture is also possible.

*Growth rate.*—Vigorous.

Stem description:

*Branch habit.*—Densely branched; average of 40 branches with an average of 4 secondary branches, and 2 tertiary branches.

*Stem size.*—Main stem; an average of 79 cm (including peduncle) in length and 6 mm in width (9 mm at base), secondary; average of 33.5 cm in length and 5 mm, tertiary; an average of 5.5 cm in length and 2 mm in width.

*Stem shape.*—Oval.

*Stem color.*—144A to 144B.

*Stem surface.*—Hairless, satiny but slightly glaucous.

Foliage description:

*Leaf shape.*—Fan-shaped in overall outline.

*Leaf division.*—3-palmate.

*Leaf internode.*—Foliage begins 33 cm from base, an average of 7 cm on main stem and an average of 5.5 cm on secondary branches.

*Leaf size.*—About 4.8 cm in length and 6.9 cm in width.

*Leaf quantity.*—About 35 per stem.

*Leaflet shape.*—Oblanceolate.

*Leaflet base.*—Cuneate.

*Leaflet apex.*—Acute.

*Leaflet venation.*—Pinnate pattern, not conspicuous, color matches leaflet color on the upper and lower surface with the mid rib on lower surface 146D.

*Leaflet margins.*—Entire.

*Leaf attachment.*—Petiolate.

*Leaf arrangement.*—Alternate.

*Leaflet surface.*—Glabrous and slightly glaucous on upper and lower surface.

*Leaflet color.*—Newly expanded and mature; upper and lower surface 137A.

*Leaflet size.*—An average of 4.8 cm in length and 1.5 cm in width.

*Petioles.*—Average of 8 mm in length and 2 mm in width, clasping to stem at mature nodes, 146D in color, surface is glabrous and satiny.

*Stipules.*—On basal 2 to 3 nodes prior to leaves; single, ovate in shape, about 3.5 cm in length and 2.9 cm in width, truncate base, 2-notched apex, 146D in color, on leave nodes; 2, lanceolate in shape, base is truncate to stem, apex is acuminate, average of 2.4 cm in length and 5 mm in width on mature leaves, 137B in color on upper surface and 137C on lower surface.

Flower description:

*Inflorescence type.*—Terminal racemes of pea-like flowers on main and secondary branches, blooms from the base to the apex.

*Inflorescence size.*—Average of 23 cm in length and 3 cm in width in mid section.

*Lastingness of inflorescence.*—3 to 4 weeks.

*Flower size.*—About 2.5 cm in depth and about 1.8 cm in diameter.

*Flower fragrance.*—Faint.

*Flower number per inflorescence.*—About 45 to 50.

*Peduncle.*—Oval in shape, up to 23 cm in length and an average of 3 mm in width, 144A to 144B in color, surface is glabrous, satiny and slightly glaucous, flower internode length averages from whorls to about 5 mm.

*Petiole.*—About 6 mm cm in length, about 1.5 mm in width, oval in shape, color a blend of 137B and N137B, glabrous and satiny surface.

*Flower buds.*—Kidney-shaped, about 2.4 cm in length and 1 cm in width, color of petal portion is a blend of 93A and 93C with veins 93A and a sliver of exposed keel portion 163C, calyx portion same as open flowers.

*Flower type.*—Papilionaceous, held at about a 45° angle.

*Calyx.*—Campanulate, about 1 cm in length and 7 mm in diameter, surface is glabrous and satiny, 144A in color suffused with N186A to 147A, persistent.

*Sepals.*—5, fused with the exception of apex of each, free portion is triangular in shape 4 mm in width and 4 mm in depth with an acute apex, 144A in color suffused with N186A to 147A.

*Corolla features.*—Papilionaceous (4 segments) with a keel, a banner and 2 lateral wings, lateral wings; obelliptic in shape, about 2.2 cm in length and 9 mm in width, color on outer surface and the inner surface is a blend of 93A and 93B with the basal portion 149D, rounded apex, oblique base, keel; only partially visible, comprised of 2 segments surrounding reproductive organs, oblong (slightly oblique) in shape with rounded apex and oblique base, 2.3 cm in length and 9 mm in width, upper surface and lower surface are 145D in color, banner; orbicular in shape, about 1.9 cm in length and 2 cm in width, upper and lower surface is a blend of 93A and 93B with the basal portion 149C to 149D and mid section marked with 192A, apex is rounded with a single notch, surface is glabrous on all sections.

*Receptacle.*—Disk-shaped, gelatinous, 144A in color, about 3 mm in diameter and 1.2 mm in depth.

Reproductive organs:

*Gynoecium.*—1 Pistil, about 2 cm in length, 1.5 mm in width; style is 144B in color and 9 mm in length; stigma minute, too small to read color, ovary is superior with a stipe, 144A in color, 7 mm in length and 1.5 mm in width; stipe is 144B in color, 3 mm in length and 1.5 mm in width.

*Androcoecium.*—10 stamens, not united, 2.5 cm in length and 1 mm in width; filament is 2.1 cm in length, 1 mm in width and 145C in color; anther is dorsifixed, 1.5 mm in length and width and 199C in color, pollen is abundant and 17A in color.

*Fruit.*—An inflated pod, technically a legume, 12 to 18 produced per inflorescence (open-pollinated) but potentially an average of 35 to 50 could be produced if all flowers were pollinated, globose-oblongoid in shape, 38 mm in length by 13 to 18 mm in width; each with a short beak approx. 2 to 3 mm in length, color of outer surface when mature in September is a color between 201A and 202A, color of inner surface 197A to 199A, walls 1.5 mm and hard at maturity, seed; 10 to 18 per fruit (open-pollinated), 165B in color, oval with the hilum side more or less straight, seed compressed to flattish, 4.5 mm in length, 3 mm in width and 2 mm in thickness.

It is claimed:

1. A new and distinct cultivar of *Baptisia* plant named 'Blueberry Sundae' as herein illustrated and described.

* * * * *